United States Patent [19]

Koch et al.

[11] 4,016,278

[45] Apr. 5, 1977

[54] PESTICIDAL CARBAMATES

[75] Inventors: Richard C. Koch, Niantic, Conn.;
Hugh C. Richards, Canterbury, England

[73] Assignee: Pfizer Inc., New York, N.Y.

[22] Filed: July 14, 1975

[21] Appl. No.: 595,535

[30] Foreign Application Priority Data

July 17, 1974 United Kingdom ............ 31612/74

[52] U.S. Cl. .................. 424/263; 260/256.5 R; 260/294.8 G; 260/304 R; 260/308 D; 424/251; 424/269; 424/270

[51] Int. Cl.² ......................................... A01N 9/22

[58] Field of Search ............. 260/294.8 G; 424/263

[56] References Cited

UNITED STATES PATENTS

| | | | |
|---|---|---|---|
| 3,033,870 | 5/1962 | Druey et al. | 260/294.8 G |
| 3,701,779 | 10/1972 | Donninger et al. | 260/294.8 G |
| 3,884,962 | 5/1975 | Koch et al. | 260/479 C |

*Primary Examiner*—Leonard Schenkman
*Attorney, Agent, or Firm*—Connolly and Hutz

[57] ABSTRACT

Novel (heterocyclicthio)phenyl N-alkylcarbamates, (heterocyclicthio)phenyl N-acyl-N-alkylcarbamates and their thionocarbamate analogs. The compounds are pesticidal agents, which are particularly suitable as ectoparasiticidal agents for use in sheep, cattle, horses, swine and the like.

10 Claims, No Drawings

PESTICIDAL CARBAMATES

BACKGROUND OF THE INVENTION

1. Field of the Invention

This invention relates to a series of (heterocyclicthio)phenyl N-alkylcarbamates, (heterocyclicthio)phenyl N-acyl-N-alkylcarbamates and their thionocarbamate analogs. The said compounds have useful pesticidal properties, and in particular they are effective in destroying the adults and/or larvae of insects and other pests which tend to infest the skins of animals, especially those of sheep, cattle, horses, swine, and the like. They are therefore especially useful as ectoparasiticidal agents for treating such animals. They are also useful as insecticides for other applications.

As a result of the breeding of adult insects and other pests on animal skins, the larvae produced tend to burrow into the skins of the afflicted animals and thereby spoil the state of the skins, with the consequence, for example, that cattle hides and sheep skins and fleece, intended for the manufacture of leather, sheepskin and woolen goods, respectively, are reduced in quality. Furthermore, the state of health and the quality of the flesh of afflicted animals may be detrimentally affected. Certain insect larvae, for example the larvae of blowflies which tend to live in sheep skin, are capable of bringing premature death to the animal if present in sufficient abundance. Tick larvae, which tend to live in cattle hides, facilitate the transmission of diseases to afflicted animals to a marked degree.

It is therefore an object of the invention to provide a series of compounds having useful pesticidal properties, in particular against insects and other pests, such as blowflies, ticks and mites, which are the cause of ectoparasitic infections of animals, as well as against household or crop insect pests, e.g. houseflies.

2. Description of the Prior Art

A number of esters of carbamic acid are known to be useful pesticides, e.g. 2-isopropoxyphenyl N-methylcarbamate, 4-(dimethylaminophenyl)-3,5-dimethylphenyl N-methylcarbamate, 1-naphthyl N-methylcarbamate, 3-(1-ethylpropyl)phenyl N-methylcarbamate and 3-(1-methylbutyl)phenyl carbamate.

Belgian Pat. No. 659,636 discloses the use of 2-(4-chlorophenoxy)-4-chlorophenyl N-methylcarbamate and 2-(4-chlorophenoxy)-4,5-dichlorophenyl N-methylcarbamate as bacteriostats and inhibitors of pathogenic mycetes. Farmacia (Bucharest), 17, 721 (1969) describes a series of 4-(phenylsulfonyl)phenyl N-substituted-carbamates, wherein the substituent is methyl, ethyl, propyl, butyl, allyl or cyclohexyl. In Farmacia (Bucharest), 18, 27 (1970), there is described a series of 4-(4-tolylsulfonyl)phenyl N-substituted-carbamates, wherein the substituent is methyl, ethyl, propyl, butyl, allyl, $C_{18}H_{37}$ or phenyl. N-acyl derivatives of aryl carbamates are described in British Pat. No. 982,235 as insecticides of reduced mammalian toxicity. West German Offenlegungsschrift No. 2,333,264 (and U.S. Pat. No. 3,884,962) disclose a variety of phenylthio-, phenylsulfinyl- and phenylsulfonyl-substituted phenyl carbamates and thionocarbamates, and N-acylated derivatives thereof.

SUMMARY OF THE INVENTION

It is an object of this invention to provide novel heterocyclicthio substituted carbamates and thionocarbamates of the formula:

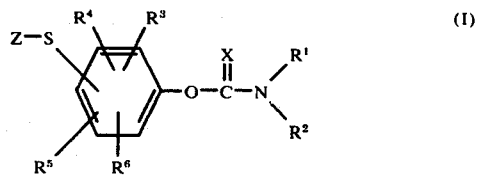

wherein $R^1$ is lower alkyl;

$R^2$ is selected from the group consisting of hydrogen, lower alkyl and an acyl group of formula $CO-R^7$;

X is selected from the group consisting of oxygen and sulfur;

$R^3$, $R^4$, $R^5$ and $R^6$ are each selected from the group consisting of hydrogen, fluoro, chloro, bromo, iodo, lower alkyl, lower alkoxy, lower alkylthio, trifluoromethyl, nitro cyano and phenyl;

and Z is selected from the group consisting of

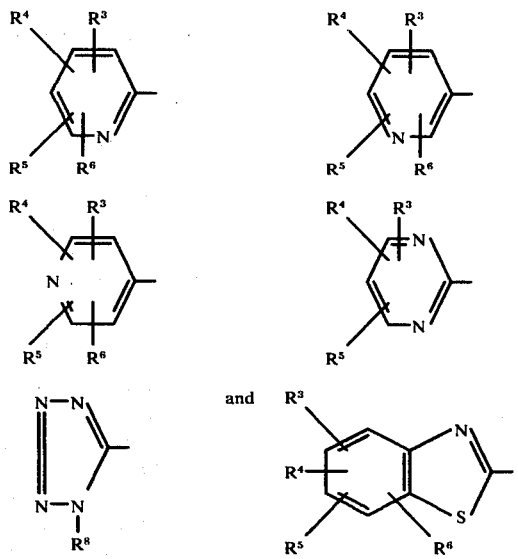

wherein $R^7$ is selected from the group consisting of hydrogen, lower alkyl, lower alkoxy-lower alkyl, lower alkylthio-lower alkyl, halo-lower alkyl, phenyllower alkyl, phenoxy-lower alkyl, phenylthio-lower alkyl and phenyl, any benzene ring therein being optionally substituted with one or more of those groups specified in the definition of $R^3$, $R^4$, $R^5$ and $R^6$;

and $R^8$ is selected from the group consisting of hydrogen, lower alkyl, phenyl and phenyl substituted by one or more lower alkyl groups.

However, the preferred compounds of this invention are those compounds of formula

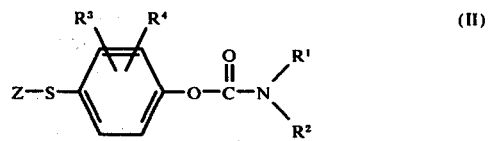

wherein $R^1$ is alkyl having from one to five carbon atoms;

$R^2$ is selected from the group consisting of hydrogen, alkyl having from one to five carbon atoms, alkanoyl having from two to five carbon atoms and chloroacetyl;

$R_3$ and $R_4$ are each selected from the group consisting of hydrogen and alkyl having from one to five carbon atoms;

and Z is selected from the group consisting of 2-pyridyl, 3-pyridyl, 4-pyridyl, 2-pyrimidyl, 4,6-dimethyl-2-pyrimidyl, 1-methyl-5-tetrazolyl and 2-benzothiazolyl.

Especially preferred compounds of the invention are the compounds of formula II, wherein $R^1$ is methyl and $R^2$ is hydrogen. Even more especially preferred compounds of the invention are the compounds of formula II, wherein $R^1$ is methyl, $R^2$ is hydrogen and $R^3$ and $R^4$ are alkyl groups (particularly methyl) at the 3- and 5-positions, respectively, relative to the O—(C=O)—$NR^1R^2$ group. The preferred Z group is 2-pyridyl.

Particularly valuable individual compounds of the invention are:

4-(2-pyridylthio)-3,5-dimethylphenyl N-methylcarbamate, 4-(2-pyrimidylthio)-3,5-dimethylphenyl N-methylcarbamate, 4-(4,6-dimethyl-2-pyrimidylthio)-3,5-dimethylphenyl N-methylcarbamate, 4-(1-methyl-5-tetrazolylthio)-3,5-dimethylphenyl Nmethylcarbamate and 4-(2-benzothiazolylthio)-3,5-dimethylphenyl N-methylcarbamate.

A further object of this invention is to provide a method of combatting ectoparasite infections of animals, which comprises administering externally to an infected animal a compound of the formula (I), as defined above.

DETAILED DESCRIPTION OF THE INVENTION

In this specification the term "halogen" means fluorine, chlorine, bromine or iodine, and "lower" when qualifying an alkyl, alkoxy or alkylthio group means that such a group contains from one to six carbon atoms. Alkyl groups containing three or more carbon atoms may be straight or branched chain alkyl groups.

The novel compounds of the invention can be prepared in a number of ways. In one method according to the invention, compounds of the formula I, wherein $R^2$ is hydrogen, can be prepared by reacting the appropriate heterocyclicthio substituted phenol of the formula

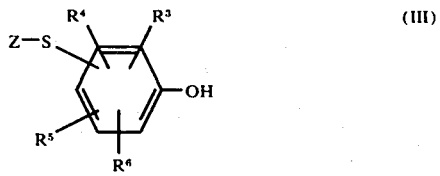

with a lower alkyl isocyanate $R^1NCO$ or isothiocyanate $R^1NCS$, suitably in solution in a reaction inert organic solvent, e.g. toluene, and in the presence of a base, e.g. triethylamine, under reflux conditions. The product is suitably recovered by removal of any undissolved solid from the cooled reaction solution by filtration and thereafter evaporating the solution in vacuo to dryness. Purification of the crude product may then be effected by recrystallization from a suitable solvent, e.g. a mixture of benzene and petroleum ether. Substituted heterocyclic-thio-phenol starting materials, which are not already known compounds, may be prepared by methods analogous to those described in the literature.

In another method according to the invention, compounds of the formula I, wherein $R^2$ is lower alkyl, can be prepared from an alkali metal derivative of the appropriate phenol of formula III, by reaction with an N,N-disubstituted carbamoyl or thiocarbamoyl chloride of the formula $R^1R^2NCXCl$. The alkali metal derivative is suitably prepared from the phenol by addition of an alkali metal compound, e.g. sodium hydride, to a solution of the phenol in a dry, reaction-inert organic solvent, e.g. dry benzene. The reaction with the substituted carbamoyl or thiocarbamoyl chloride is suitably performed by adding the latter to the reaction mixture of alkali metal compound and phenol derivative in the solution after formation of the alkali metal derivative, and then refluxing the mixture for several hours. Isolation of the product may be effected by adding the cooled reaction mixture to water, separating the organic layer and washing, drying and evaporating it in vacuo to dryness, and purification may then be performed by conventional techniques.

Also according to the invention, compounds of the formula I, wherein $R^2$ is acyl, can be prepared from the corresponding compound of formula I, wherein $R^2$ is hydrogen, by conventional acylation techniques using such acylating agents as the appropriate acyl halide or carboxylic acid anhydride. In some cases where the acyl halide is used as the acylating agent, it is advantageous to form the sodio derivative of the starting material e.g. by addition of sodamide to a solution of the compound in a dry reaction inert organic solvent, e.g. dry toluene, before reacting with the acyl halide.

The compounds of the invention are potent pesticidal agents. This can be shown in tests in which their insecticidal and acaricidal properties towards houseflies, blowflies and ticks of various stages of maturity are measured.

In one test, 2- 4-day old females of the World Health Organization standard fully susceptible strain *Musca domestica* (common housefly) are anesthetized with carbon dioxide and then each contacted on the dorsal surface of the thorax with one microgram of the test compound contained in 1 microliter of solution, using e.g. acetone, methanol or methyl ethyl ketone as the solvent. The flies are then maintained for 24 hours in gauze-covered pots at 25° C. and at about 50% relative humidity with a cotton wool pad, moistened with sugar solution as a source of food, placed on the gauze. Contacted with an equivalent volume of solvent only are the same number of anesthetized control flies. At the end of the 24-hour period, the mortality is noted and recorded as a percentage, after correction for any mortality among the controls. The result gives a measure of the effectiveness of the test compound applied topically.

In order to test the effectiveness of the compounds when used as bait for adult blow-flies, two groups of adult female *Lucilia sericata* are maintained for 24 hours in pots each containing sugar and a pad of wet cotton wool as a free water supply, one of the sugar supplies being impregnated with test compound to the extent of 100 p.p.m. The mortality is noted as in the previous test and recorded as a corrected percentage.

Larvicidal properties are investigated by maintaining test and control groups of *Lucilia sericata* (blowfly) larvae in separate test tubes, each containing filter paper partially soaked in calf serum serving as food and plugged with cotton wool. The filter paper in the test tube containing the test larvae is additionally impregnated with the compound under investigation to the extent of a 100 mg./m² deposition. Both test tubes are stored with the top part only in a strong light so as to induce the larvae to stay in the lower part of the tubes in contact with the filter paper through exploitation of their aversion to light. As in previous tests, mortality is noted and recorded as a corrected percentage. The finding of substantial numbers of test larvae on the illuminated plug suggests that the test compound has marked repellant properties.

Effectiveness against tick nymphs is measured using a similar procedure to the previous test described, the principal differences being that the filter papers used are not impregnated with any food material, all the ticks are unfed, and the containing vessels used are glass jars. A result in the form of a corrected percentage figure is again obtained for each compound.

In addition to percentage effectiveness figures, $ED_{50}$ results can be obtained from dose response measurements using any of the aforedescribed tests.

The compounds of the invention when used for treating ectoparasitic infections of animals such as sheep and cattle are suitably administered in the form of dusts or wettable powders, or as dips or sprays comprising an aqueous emulsion of an emulsifiable concentrate. The latter can be, for example, a 5–40% (g./100 ml.) solution of the compound in a non-toxic organic solvent containing an emulsifying agent, and this is diluted with water to give a concentration of the compound in the aqueous medium of from 0.005 to 0.1% w/v (g./100 ml.), or approximately 50 to 1000 p.p.m. The said organic solvent is substantially water-immiscible, and suitable solvents include toluene, xylene and petroleum oil or an alkylated naphthalene. The volatile solvents, e.g. toluene and xylene, evaporate after spraying to leave a deposit of the active ingredient. Suitable emulsifiers, which can be cationic, anionic or non-ionic, as is well known to those skilled in the art, include ordinary soaps (anionic), lauryl pyridinium chloride (cationic) and polyoxyethylene lauryl ethers (non-ionic), the latter being, for example, a reaction product of ethylene oxide (10 moles) with dodecyl alcohol (1 mole). The madeup spray or dip can be an emulsion, slurry or solution.

A dust is made by mixing the appropriate amount of active ingredient with a diluent or carrier such as talc, clay, calcite, pyrophyllite, diatomaceous earth, walnut shell flour, silica gel, hydrated alumina or calcium silicate to afford a concentration of active ingredient of from about 0.25 to about 4% by weight. As an alternative method of preparation, the diluent or carrier is mixed with a solution of the active ingredient in a volatile organic solvent, e.g. benzene or acetone. The solvent is then removed by evaporation and the mixture ground.

Wettable powders, of special value for spray applications, are made by adding suitable wetting agents and conditioning agents to the dusts. They usually contain from about 25% to about 75% w/v of active ingredient.

The following Examples are provided solely for the purpose of further illustration.

EXAMPLE I 4-(2-Pyridylthio)-3,5-dimethylphenyl N-Methylcarbamate

A. To a stirred solution of 3,5-dimethylphenol (122 g.) in anhydrous tetrahydrofuran (1000 ml.) containing aluminum chloride (1 g.) was slowly added a suspension of 2-pyridylsulphenyl chloride [the product obtained from chlorination of a solution of di-2-pyridyl disulphide (110 g.) in carbon tetrachloride (1000 ml.)] in carbon tetrachloride (200 ml.) and anhydrous tetrahydrofuran (100 ml.). During the addition a further 650 ml. of carbon tetrachloride was added as diluent to facilitate agitation. When addition was complete, the reaction was heated to reflux and held at this temperature for 2.5 hrs. Heating was then stopped and the reaction was allowed to cool overnight with stirring. The resulting precipitate was removed by filtration and washed thoroughly with ether, and was then taken up in water. Solid sodium bicarbonate was then added to neutralization point and the resulting solid was extracted into an ethyl acetate-acetone mixture (1:1). After drying the extract, (MgSO$_4$) the solvent was removed to yield 4-(2-pyridylthio)-3,5-dimethylphenol as a colorless solid (155 g.). A sample was purified by chromatography on alumina, and had melting point 189.5°–190.5° C.

Analysis: Calc'd for $C_{13}H_{13}NOS$: C, 67.50; H, 5.66; N, 6.06 (%): Found: C, 67.27; H, 5.71; N, 5.98 (%).

B. 4-(2-Pyridylthio)-3,5-dimethylphenol (161 g.), prepared in part A, and methylisocyanate (48 g.) was dissolved in dry toluene (1500 ml.) containing triethylamine (10 ml.) and the mixture was then stirred under reflux overnight. Further quantities of methyl isocyanate (22 g.) and triethylamine (10 ml.) were then added and refluxing was continued for a further 6 hours.

Removal of solvent in vacuo afforded a solid which was recrystallized from benzene/petroleum ether (b.p. 60°–80° C.) (9:5), to yield 144 g. of 4-(2-pyridylthio)-3,5-dimethylphenyl N-methyl carbamate of melting point 130°–132° C.

Analysis: Calc'd for $C_{15}H_{16}N_2O_2S$: C, 62.48; H, 5.59; N, 9.71 (%) Found: C, 62.22; H, 5.78; N, 10.14 (%).

EXAMPLE II

The following compounds were prepared by procedures analogous to that of Example I, but using the appropriate sulfenyl chloride in place of the 2-pyridylsulfenyl chloride:

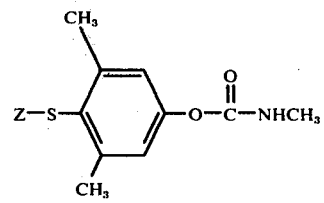

| | | Analysis | | | | | |
|---|---|---|---|---|---|---|---|
| | | Calc'd | | | Found | | |
| Z | m.p. (° C.) | C | H | N | C | H | N |
| 2-benzothiazolyl | 117–119 | 59.28 | 4.68 | 8.13 | 58.94 | 4.68 | 7.97 |

| | | Analysis | | | | | |
|---|---|---|---|---|---|---|---|
| | m.p. | Calc'd | | | Found | | |
| Z | (° C.) | C | H | N | C | H | N |
| 2-pyrimidyl | 141–142 | 58.11 | 5.19 | 14.54 | 58.01 | 5.20 | 14.65 |
| 4,6-dimethyl-2-pyrimidyl | 116–118 | 60.56 | 6.00 | 13.56 | 60.25 | 6.03 | 13.47 |
| 1-methyl-5-tetrazolyl | 141–142 | 49.13 | 5.15 | 23.87 | 49.17 | 5.21 | 24.27 |

EXAMPLE III

The following compounds are prepared according to the procedure of Example I, by using the appropriate phenol and sulfenyl chloride in Part A, and the appropriate 4-(heterocyclicthio)phenol and alkyl isocyanate in Part B:

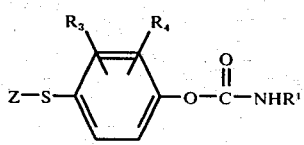

| Z | $R^3$ | $R^4$ | $R^1$ |
|---|---|---|---|
| 2-pyridyl | H | 3-CH$_3$ | CH$_3$ |
| 2-pyridyl | H | 2-CH$_3$CH$_2$ | CH$_3$CH$_2$CH$_2$ |
| 2-pyridyl | H | 3-(CH$_3$)$_2$CHCH$_2$CH$_2$ | CH$_3$ |
| 2-pyridyl | 2-CH$_3$ | H | CH$_3$(CH$_2$)$_2$CH$_2$ |
| 2-pyridyl | 3-CH$_3$CH$_2$CH$_2$ | H | CH$_3$ |
| 2-pyridyl | 3-CH$_3$CH$_2$CH$_2$CH$_2$ | H | CH$_3$ |
| 2-pyridyl | 3-CH$_3$ | 5-CH$_3$ | CH$_3$(CH$_2$)$_3$CH$_2$ |
| 2-pyridyl | 2-CH$_3$CH$_2$ | 3-CH$_3$CH$_2$ | CH$_3$ |
| 2-pyridyl | 2-CH$_3$ | 3-(CH$_3$)$_2$CH | CH$_3$ |
| 3-pyridyl | H | H | CH$_3$CH$_2$ |
| 3-pyridyl | 3-CH$_3$CH$_2$ | H | (CH$_3$)$_2$CH |
| 3-pyridyl | 3-CH$_3$ | 5-CH$_3$ | CH$_3$ |
| 4-pyridyl | H | H | CH$_3$CH$_2$ |
| 4-pyridyl | 5-CH$_3$ | 3-CH$_3$ | CH$_3$ |
| 2-pyrimidyl | 2-CH$_3$CH$_2$CH$_2$ | H | (CH$_3$)$_2$CHCH$_2$ |
| 2-pyrimidyl | 3-CH$_3$CH$_2$ | 5-CH$_3$CH$_2$ | CH$_3$ |
| 4,6-dimethyl-2-pyrimidyl | H | H | CH$_3$ |
| 4,6-dimethyl-2-pyrimidyl | H | 3-CH$_3$ | CH$_3$CH$_2$ |
| 1-methyl-5-tetrazolyl | H | H | CH$_3$ |
| 1-methyl-5-tetrazolyl | 3-CH$_3$ | H | CH$_3$CH$_2$CH$_2$ |
| 1-methyl-5-tetrazolyl | 3-CH$_3$CH$_2$ | 5-CH$_3$CH$_2$ | CH$_3$CH$_2$ |
| 1-methyl-5-tetrazolyl | 3-CH$_3$ | 5-CH$_3$CH$_2$ | CH$_3$ |
| 2-benzothiazolyl | H | H | CH$_3$ |
| 2-benzothiazolyl | 3-CH$_3$(CH$_2$)$_3$CH$_2$ | H | CH$_3$CH$_2$CH$_2$ |
| 2-benzothiazolyl | 2-CH$_3$ | 5-CH$_3$ | CH$_3$(CH$_2$)$_3$CH$_2$ |
| 2-benzothiazolyl | 3-CH$_3$ | 5-CH$_3$ | CH$_3$ |

EXAMPLE IV

3,5-Dimethyl-4-(2-pyridylthio)phenyl N,N-Dimethylcarbamate

To a stirred suspension of 240 mg. of sodium hydride in 20 ml. of dry tetrahydrofuran is added a solution of 2.31 g. of 3,5-dimethyl-4-(2-pyridylthio)phenol in 30 ml. of dry tetrahydrofuran. After the effervescence has subsided, a solution of 1.1 g. of N,N-dimethylcarbamoyl chloride in 10 ml. of dry tetrahydrofuran is added dropwise. The reaction mixture is stirred at ambient temperature for 16 hours, and then under reflux for 4 hours. The reaction mixture is cooled to room temperature, and then diluted with an excess of water. The product is extracted into ethyl acetate. The ethyl acetate is washed with water, dried using anhydrous magnesium sulfate, and then evaporated in vacuo to give crude 3,5-dimethyl-4-(2-pyridylthio)phenyl N,N-dimethylcarbamate. The crude product can be purified further by recrystallization.

EXAMPLE V

The following compounds are prepared by reaction of the appropriate 4-(heterocyclicthio)phenol with the requisite carbamoyl chloride, using the procedure of Example IV:

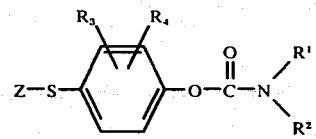

| Z | $R^3$ | $R^4$ | $R^1$ | $R^2$ |
|---|---|---|---|---|
| 2-pyridyl | H | 3-CH$_3$ | CH$_3$ | CH$_3$ |
| 2-pyridyl | H | H | CH$_3$CH$_2$ | CH$_3$CH$_2$ |
| 2-pyridyl | 3-CH$_3$ | 5-CH$_3$ | CH$_3$ | CH$_3$(CH$_2$)$_3$CH$_2$ |
| 3-pyridyl | 2-CH$_3$ | 5-CH$_3$ | CH$_3$ | (CH$_3$)$_2$CH |
| 3-pyridyl | 3-CH$_3$CH$_2$ | 5-CH$_3$CH$_2$ | CH$_3$ | CH$_3$(CH$_2$)$_2$CH$_2$ |
| 4-pyridyl | 3-CH$_3$ | 5-CH$_3$ | CH$_3$ | CH$_3$ |
| 4-pyridyl | H | H | CH$_3$CH$_2$ | CH$_3$CH$_2$ |
| 2-pyrimidyl | H | 3-CH$_3$ | CH$_3$ | CH$_3$ |

| Z | R³ | R⁴ | R¹ | R² |
| --- | --- | --- | --- | --- |
| 4,6-dimethyl-2-pyrimidyl | H | H | CH₃ | (CH₃)₂CH |
| 1-methyl-5-tetrazolyl | 3-CH₃ | 3-CH₃ | CH₃ | CH₃ |
| 1-methyl-5-tetrazolyl | 3-(CH₃)₂CH | H | CH₃ | CH₃CH₂ |
| 2-benzothiazolyl | 3-CH₃ | 3-CH₃ | CH₃ | CH₃ |
| 2-benzothiazolyl | 2-CH₃CH₂ | H | CH₃CH₂ | CH₃(CH₂)₂CH₂ |

EXAMPLE VI

3,5-Dimethyl-4-(2-pyridylthio)phenyl N-acetyl-N-methylcarbamate

A mixture of 3.04 g. of 3,5-dimethyl-4-(2-pyridylthio)phenyl N-methylcarbamate, 30 ml. of acetic anhydride and 1.2 g. of concentrated sulfuric acid is heated under reflux for 20 minutes. To the cooled solution is then added 3.0 g. of sodium acetate, to neutralize the sulfuric acid. The reaction mixture is diluted with an excess of diethyl ether, and the solid which precipitates is removed by filtration. The filtrate is evaporated to dryness in vacuo, leaving crude 3,5-dimethyl-4-(2-pyridylthio)phenyl N-acetyl-N-methylcarbamate. The crude product is purified further by recrystallization.

EXAMPLE VII

Starting with the appropriate 4-(heterocyclicthio)-phenyl N-alkylcarbamate and the requisite carboxylic acid anhydride, and using the method of Example VI, the following compounds are prepared:

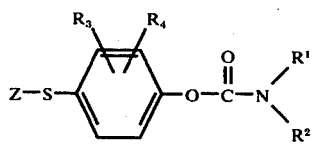

| Z | R³ | R⁴ | R¹ | R² |
| --- | --- | --- | --- | --- |
| 2-pyridyl | H | 3-CH₃ | CH₃ | CH₃-CO |
| 2-pyridyl | 3-CH₃CH₂CH₂ | H | CH₃ | CH₃CH₂-CO |
| 2-pyridyl | 3-CH₃ | 5-CH₃ | CH₃(CH₃)₃CH₂ | CH₃-CO |
| 3-pyridyl | H | H | CH₃CH₂ | CH₃(CH₂)₃-CO |
| 3-pyridyl | 3-CH₃ | 5-CH₃ | CH₃ | CH₃-CO |
| 4-pyridyl | 5-CH₃ | 3-CH₃ | CH₃ | CH₃-CO |
| 4-pyridyl | H | H | CH₃CH₂ | (CH₃)₂CH-CO |
| 2-pyrimidyl | 3-CH₃CH₂ | 5-CH₃CH₂ | CH₃ | CH₃-CO |
| 4,6-dimethyl-2-pyrimidyl | H | 3-CH₃ | CH₃CH₂ | CH₃-CO |
| 1-methyl-5-tetrazolyl | H | H | CH₃ | CH₃CH₂CH₂-CO |
| 1-methyl-5-tetrazolyl | 3-CH₃ | 5-CH₃CH₂ | CH₃ | CH₃-CO |
| 2-benzothiazolyl | 3-CH₃(CH₂)₃CH₂ | H | CH₃CH₂CH₂ | CH₃CH₂-CO |
| 2-benzothiazolyl | 3-CH₃ | 5-CH₃ | CH₃ | CH₃-CO |
| 2-pyridyl | 3-CH₃ | 5-CH₃ | CH₃ | Cl-CH₂-CO |
| 2-pyrimidyl | 3-CH₃ | 5-CH₃ | CH₃ | Cl-CH₂-CO |
| 1-methyl-5-tetrazolyl | 5-CH₃ | 3-CH₃ | CH₃CH₂ | Cl-CH₂-CO |
| 2-benzothiazolyl | 3-CH₃ | H | CH₃ | Cl-CH₂-CO |

EXAMPLE VIII

The constituents of an emulsifiable concentrate were as follows:

4-(2-pyridylthio)-3,5-dimethylphenyl N-methylcarbamate (compound of Example I): 5.0% w/v
Arylan CA - (calcium dodecyl benzene sulphonate in an alcoholic solvent): 3.5% w/v
Ethylan BV - (alkyl phenol polyglycol ether): 1.5% w/v
Aromasol H - (mixed hydrocarbon solvent) to 100%

("Arylan", "Ethylan" and Aromasol" are Trade Marks)

The emulsifying agents Arylan CA and Ethylan BV, and the solvent Aromasol H were admixed and stirred until homogeneous, and the compound of the invention was then added. Stirring was continued until the compound had completely dissolved in the medium.

The concentrate is suitably diluted with water, thus affording an aqueous emulsion, before administration as a dip or spray to infected animals.

What is claimed is:

1. A compound of the formula

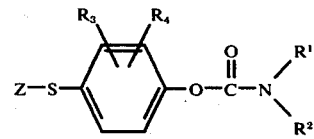

wherein R¹ is alkyl having from one to five carbon atoms;
R² is selected from the group consisting of hydrogen, alkyl having from one to five carbon atoms, alkanoyl having from two to five carbon atoms and chloroacetyl;
R³ and R⁴ are each selected from the group consisting of hydrogen and alkyl having from one to five carbon atoms;

and Z is selected from the group consisting of 2-pyridyl, 3-pyridyl and 4-pyridyl.

2. A compound according to claim 1, wherein R² is hydrogen.

3. A compound according to claim 2, wherein R¹ is methyl

4. A compound according to claim 3, wherein R³ is alkyl and is at the 3-position relative to the O—(C=O)—NR¹R² group, and R⁴ is alkyl and is at the 5-position relative to the O—(C=O)—NR¹R² group.

5. A compound according to claim 4, wherein R³ is 3-methyl and R⁴ is 5-methyl.

6. The compound according to claim 5, wherein Z is 2-pyridyl.

7. A composition suitable for use as an insecticide and acaricide concentrate which comprises a non-toxic organic solvent, from 5 to 40 g. per 100 ml. of solvent of an emulsifying agent and from 5 to 40 g. per 100 ml. of solvent of at least one compound of the formula

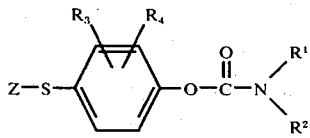

wherein $R^1$ is alkyl having from one to five carbon atoms;

$R^2$ is selected from the group consisting of hydrogen, alkyl having from one to five carbon atoms, alkanoyl having from two to five carbon atoms and chloroacetyl;

$R^3$ and $R^4$ are each selected from the group consisting of hydrogen and alkyl having from one to five carbon atoms;

and Z is selected from the group consisting of 2-pyridyl, 3-pyridyl and 4-pyridyl.

8. A method of treating ectoparasite infections of animals, which comprises administering, externally, to an infected animal, an ectoparasiticidal effective amount of a compound of the formula

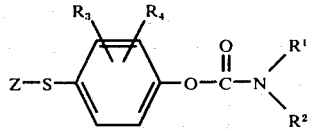

wherein $R^1$ is alkyl having from one to five carbon atoms;

$R^2$ is selected from the group consisting of hydrogen, alkyl having from one to five carbon atoms, alkanoyl having from two to five carbon atoms and chloroacetyl;

$R^3$ and $R^4$ are each selected from the group consisting of hydrogen and alkyl having from one to five carbon atoms;

and Z is selected from the group consisting of 2-pyridyl, 3-pyridyl and 4-pyridyl.

9. The method according to claim 8, wherein $R^2$ is hydrogen, $R^3$ is 3-methyl and $R^4$ is 5-methyl.

10. The method according to claim 9, wherein $R^1$ is methyl and Z is 2-pyridyl.

* * * * *